(12) United States Patent
Balan et al.

(10) Patent No.: US 7,194,062 B2
(45) Date of Patent: Mar. 20, 2007

(54) GAMMA CAMERA AND CT SYSTEM

(75) Inventors: Adi Balan, Haifa (IL); Yigal Shrem, Haifa (IL); Albert Lonn, Beaconsfield (GB); Benny Hajaj, Zoran (IL); Naor Wainer, Zichron-Yaakov (IL); Yaron Hefetz, Herzelia (IL); Gideon Berlad, Haifa (IL); Leonid Yakubovsky, Kiryat-Bialik (IL)

(73) Assignee: Elgems Ltd., Tirat HaCarmel (IL)

( * ) Notice: Subject to any disclaimer, the term of this patent is extended or adjusted under 35 U.S.C. 154(b) by 0 days.

(21) Appl. No.: 11/217,644

(22) Filed: Aug. 31, 2005

(65) Prior Publication Data

US 2006/0050839 A1    Mar. 9, 2006

Related U.S. Application Data

(62) Division of application No. 11/044,772, filed on Jan. 26, 2005, which is a division of application No. 10/900,936, filed on Jul. 28, 2004, now Pat. No. 6,878,941, which is a division of application No. 10/009,375, filed as application No. PCT/IL99/00300 on Jun. 6, 1999, now Pat. No. 6,841,782.

(51) Int. Cl.
*A61B 6/00* (2006.01)
*A61B 6/08* (2006.01)

(52) U.S. Cl. .......................................... 378/15; 378/205

(58) Field of Classification Search .................... 378/4, 378/15, 19, 193–198, 205
See application file for complete search history.

(56) References Cited

U.S. PATENT DOCUMENTS

| 4,014,109 | A |   | 3/1977  | Schramm |
|-----------|---|---|---------|---------|
| 4,115,695 | A | * | 9/1978  | Kelman ........................ 378/17 |
| 4,499,375 | A |   | 2/1985  | Jaszczak |
| 4,578,585 | A |   | 3/1986  | Gosis et al. |
| 4,585,008 | A |   | 4/1986  | Jarkewicz |
| 4,630,202 | A |   | 12/1986 | Mori |
| 5,289,008 | A |   | 2/1994  | Jaszczak et al. |
| 5,296,708 | A |   | 3/1994  | Moyers et al. |
| 5,354,993 | A | * | 10/1994 | Kedmi et al. ................ 250/551 |

(Continued)

FOREIGN PATENT DOCUMENTS

DE    198 35 451    3/1999

(Continued)

OTHER PUBLICATIONS

IMPACTSCAN.ORG "The GE Millennium VG Hawkeye SPECT/CT scanner"; impactscan.org/rsna.

(Continued)

*Primary Examiner*—Edward J. Glick
*Assistant Examiner*—Irakli Kiknadze

(57) ABSTRACT

A method of mounting a CT imager on a gantry: determining a center of rotation of a rotor of the gantry; siting a plurality of mounting elements at predetermined positions with respect to the center of rotation; and attaching the mounting elements to the rotor while keeping the mounting elements at the predetermined positions.

13 Claims, 10 Drawing Sheets

U.S. PATENT DOCUMENTS

| | | | |
|---|---|---|---|
| 5,376,795 | A | 12/1994 | Hasegawa et al. |
| 5,391,877 | A | 2/1995 | Marks |
| 5,438,602 | A | 8/1995 | Crawford et al. |
| 5,471,061 | A | 11/1995 | Moyers et al. |
| 5,481,115 | A | 1/1996 | Hsieh et al. |
| 5,554,848 | A | 9/1996 | Hermony et al. |
| 5,565,684 | A | 10/1996 | Gullberg et al. |
| 5,598,003 | A | 1/1997 | Jones et al. |
| 5,681,985 | A * | 10/1997 | Selby ........................ 73/54.28 |
| 5,682,036 | A | 10/1997 | Hines et al. |
| 5,717,212 | A | 2/1998 | Fulton et al. |
| 5,750,991 | A | 5/1998 | Moyers et al. |
| 5,803,914 | A | 9/1998 | Ryals et al. |
| 5,838,009 | A | 11/1998 | Plummer et al. |
| 5,900,636 | A | 5/1999 | Nellemann et al. |
| 6,040,580 | A | 3/2000 | Watson et al. |
| 6,171,243 | B1 | 1/2001 | Gagnon et al. |
| 6,194,724 | B1 | 2/2001 | Kaoukab Raji |
| 6,205,347 | B1 | 3/2001 | Morgan et al. |
| 6,232,605 | B1 | 5/2001 | Soluri et al. |
| 6,429,433 | B1 | 8/2002 | Gagnon et al. |
| 6,490,476 | B1 | 12/2002 | Townsend et al. |
| 6,539,103 | B1 | 3/2003 | Panin et al. |
| 6,628,983 | B1 | 9/2003 | Gagnon |
| 6,631,284 | B2 | 10/2003 | Nutt et al. |
| 6,787,777 | B1 | 9/2004 | Gagnon et al. |

FOREIGN PATENT DOCUMENTS

| | | |
|---|---|---|
| WO | WO 91/00048 | 1/1991 |
| WO | WO 95/35509 | 12/1995 |
| WO | WO 98/33076 | 7/1998 |
| WO | WO 98/54598 | 12/1998 |

OTHER PUBLICATIONS

Beyer T. et al.; "Optimization Of Transmission and Emission Scan Duration In 3D Whore-Body Pet" IEEE Inc. New York, US, Nov. 7, 1996, pp. 1362-1366, XP001146664.

JP 08-243100 A; Sep. 24, 1996; Azemoto, S. & Patent Abstracts of Japan; vol. 1997; No. 01; Jan. 31, 1997.

JP 09-154838 A; Jun. 17, 1997; Taguchi, T. & Patent Abstracts of Japan; vol. 1997; No. 10; Oct. 31, 1997.

Dilmanian, F. A. et al.; "Dual Energy Iodine Contrast CT with Monochromatic X Rays;" Oct. 21-28, 1995; 1995 IEEE Nuclear Science Symposium and Medical Imaging Conference Record; San Francisco; New York, US; vol. 3; pp. 1392-1396; XP000632544.

Beyer, T. et al.; "Optimization of Transmission and Emission Scan Duration in 3D Whole-Body PET;" Nov. 7, 1996; IEEE Transactions on Nuclear Science; IEEE Inc.; New York, US; pp. 1362-1366; XP001146664.

Beyer, T. et al.; "The Use of X-Ray CT for Attenuation Correction of PET Data;" Oct. 30, 1994-Nov. 5, 1994; Nuclear Science Symposium and Medical Imaging Conference; No. 4; Norfolk, VA, US; pp. 1573-1577; XP002257689.

Townsend, D. W. et al.; "The SMART scanner: a combined PET/CT tomograph for clinical oncology;" Nov. 8-14, 1998; IEEE Nuclear Science Symposium Conference Record; pp. 1170-1174; XP001146665; Toronto, Ont. Canada.

* cited by examiner

US 7,194,062 B2

GAMMA CAMERA AND CT SYSTEM

RELATED APPLICATIONS

The present application is a divisional application of U.S. application Ser. No. 11/044,772, filed on Jan. 26, 2005 which is a divisional application of U.S. application Ser. No. 10/900,936, filed on Jul. 28, 2004, now U.S. Pat. No. 6,878,941, which is a divisional application of U.S. application Ser. No. 10/009,375, filed on Apr. 9, 2002, now U.S. Pat. No. 6,841,782, which is a U.S. national application of PCT Application No. PCT/IL99/00300, published as WO 00/75691, filed on Jun. 6, 1999.

FIELD OF THE INVENTION

The present invention is related to the field of nuclear medicine and in particular to gamma cameras with x-ray transmission imaging for localization and attenuation correction of nuclear images.

BACKGROUND OF THE INVENTION

Attenuation correction in nuclear medicine imaging is well known in the art. In particular, it is well known when producing SPECT or PET images to correct the images for the effect of attenuation of the gamma rays used for producing the image by intervening tissue and bone. In particular, it is known to generate an attenuation map (three dimensional image or a series of two dimensional slices) of the region being imaged by the gamma camera and correcting the counts of gamma events based on the attenuation of the tissue and bone between the source of the gamma ray and the detector.

The attenuation image is produced in some prior art devices using a source of gamma rays to produce a nuclear CT (attenuation) image. X-ray based CT attenuation images are used in other prior art devices. Devices which utilize the same detector for acquiring both emission and transmission images have been reported as well as devices which utilize different detectors for acquiring the images. Devices utilizing both single and multiple detectors for acquisition of one or both of the images are also known.

In general, prior art devices which utilize X-rays for producing the attenuation map use separate gantries for the X-ray and gamma ray imaging sub-systems. Systems of this type are described, for example, in U.S. Pat. No. 5,391,877, the disclosure of which is incorporated herein by reference. However, this requires matching between the attenuation maps and the nuclear medicine images. Other systems utilize the same gantry for both the X-ray and gamma ray imaging systems. Such systems are described for example in U.S. Pat. No. 5,376,795, the disclosure of which is incorporated herein by reference.

SUMMARY OF THE INVENTION

An aspect of some preferred embodiments of the invention is concerned with a system which has PET, SPECT and X-ray CT capabilities. In preferred embodiments according to this aspect, the system can perform either x-ray, SPECT or PET three dimensional imaging (or multiple slices of two dimensions).

An aspect of some preferred embodiments of the invention is concerned with the relative speeds of detector rotation of gamma camera heads for the acquisition of data for SPECT imaging and of X-ray detectors for acquisition of data for CT reconstruction for the attenuation correction map. In particular, in accordance with some preferred embodiments of the invention, the CT image is acquired at a low rotation rate, comparable to the rate of rotation of the gamma camera heads. Alternatively, but less preferably, the X-ray data is acquired at a high rotation rate, and preferably over several rotations. The data from the same angle for the various rotations is then averaged. Additionally or alternatively, lower quality CT data is acquired to match the Gamma camera resolution and noise level.

This allows for three important advantages. Firstly, this allows for matching between the conditions under which the data is acquired, i.e., the same averaging of body motion is intrinsic for both acquisitions. Second, a slow rotation rate gantry may be used. Third, lower X-ray power may be used. This allows for a smaller power supply and for a smaller gantry, of the size and type normally suitable for gamma cameras alone.

In some preferred embodiments of the invention, the power of the X-ray energy is adjusted to provide an optimum energy per view by operating in a pulsed mode, in which the pulse duty cycle is designed to give a desired signal to noise in X-ray data. The data may also be adjusted by providing quasi DC to the X-ray tube. That is to say, the duration of the X-ray is controlled to be sufficient to provide the desired total X-ray energy.

An aspect of some preferred embodiments of the invention is concerned with a gamma camera which can create transmission and attenuation maps utilizing two detectors oriented 90° degrees apart, 180° apart or at any selectable angle between 90° and 180°.

An aspect of some preferred embodiments of the invention is concerned with the reduction of the amount of radiation utilized for the acquisition of the attenuation image. In accordance with a preferred embodiment of the invention, the NM image is acquired first. Then data for the attenuation image is acquired only over a range of the patient's body for which the NM image is of interest. In particular, the attenuation image is acquired only for a region containing organs of interest (as identified from the NM image) or, over regions of the body for which activity is identified in the NM image.

An aspect of some preferred embodiments of the invention is concerned with the electrification of the X-ray system and the Gamma camera heads. In accordance with a preferred embodiment of the invention, a common set of conduits supplies power to the X-ray system and the Gamma camera heads. In some preferred embodiments of the invention, the X-ray generator used for attenuation data acquisition, including its power supply, are mounted on the gantry, such that only low voltage need be transferred to the rotating gantry. This transfer may be achieved by using slip rings or long coiled cables.

An aspect of some preferred embodiments of the invention is concerned with the transfer of data from X-ray detectors and Gamma ray detectors to an image reconstruction system. In a preferred embodiment of the invention the outputs of the X-ray detectors and the gamma camera head or heads is digitized. The digitized signals are sent, via a common data transmission line or lines to a common computer system. In a preferred embodiment of the invention, the data is transmitted by a common conductor or optical cable system. In another preferred embodiment, the data is transmitted by a wireless link, for example an optical link or a radio link.

In a related aspect of some preferred embodiments of the invention, the same computer infrastructure, such as reconstruction algorithms and/or a common CPU is used to reconstruct both NM and X-ray images.

An aspect of some preferred embodiments of the invention is concerned with a combined NM and X-ray CT system which operates in one or more of a plurality of modes. For example, some possible modes are:

1) An ungated NM imaging mode, in which the X-ray detectors rotate together with the NM detectors or in which the X-ray detectors make a number of rotations and the data from the same view for different rotations is averaged.

2) A respiration gated NM imaging mode in which the CT data is acquired in a high rotation rate mode, and the data from each view is associated with one of the respiration gated time periods. In this mode, unaveraged CT data may be used to generate a higher resolution, if noisier image.

3) A respiration gated NM imaging mode in which CT data is acquired over one or a very few rotations while the patient holds his breath. The CT image is then used to correct an NM image that corresponds to this condition.

4) A cardiac gated NM imaging mode in which the CT data is acquired either in a slow rotation rate mode or in a fast rotation rate mode, with averaging of the data. In this mode, the attenuation data is not correlated with the cardiac cycle. However, the CT image is based on averaged data over the cardiac cycle.

5) A cardiac gated NM imaging mode in which the CT data is acquired in a fast rotation rate mode with gating of the CT data in accordance with the same binning as the NM data.

An aspect of some preferred embodiments of the invention is concerned with the construction of a combined NM/X-ray CT system. In some preferred embodiments of the invention, the relationship between the X-ray and NM systems are fixed with respect to rotational position. This system, while structurally simple, must take data for the X-ray and NM images separately, unless the rotation rate for the two is the same as in some of the above modes of operation. In some preferred embodiments of the invention, a single main gantry is provided. One of the two sets of data acquisition systems rotates with the main gantry. The second acquisition system is mounted on and rotates with respect to the main gantry.

An aspect of some preferred embodiments of the invention involves the alignment and calibration of a combined CT/NM imaging system. In preferred embodiments of the invention, the structure of the CT portion of the system is very simple as compared with dedicated CT systems, since the alignment and power requirements and the weight of the system are all greatly reduced. In order to simplify the adjustment of the X-ray system and especially the field replacement of the X-ray system, a method of alignment based on a standard alignment surface and position and a method of providing these surfaces without accurate machining of these surfaces. In a preferred embodiment of the invention, the alignment surfaces are mounted onto the gantry by screws, based on a position determined by an alignment jig centered at the center of rotation of the gantry. More preferably, the alignment surfaces are attached to the gantry by glue. Due to the relatively light weight of the X-ray system, these mounting methods are both efficient and secure.

In a preferred embodiment of the invention, the X-ray system and the NM system are axially displaced (along the axis of rotation). Preferably, the X-ray system is mounted closer to gantry support that is the NM system.

There is thus provided in accordance with a preferred embodiment of the invention, a method of producing a nuclear medicine image of a subject, comprising:

acquiring nuclear imaging data suitable to produce a nuclear tomographic image, said nuclear image data being acquired by a gamma camera head rotating about the subject at an average first rate;

acquiring x-ray imaging data suitable to produce an x-ray tomographic image for attenuation correction of the gamma camera image, said X-ray imaging data being acquired by detectors irradiated by an X-ray source rotating around the subject at an average second rate, said second rate being within a factor of 10 of the first rate; and reconstructing an attenuation corrected nuclear medicine image utilizing the nuclear imaging data and x-ray imaging data. Preferably, the second rate and the first rate are substantially the same. Preferably, the first and second rates are the same.

There is also provided in accordance with a preferred embodiment of the invention, a method of producing a nuclear medicine image of a subject, comprising:

acquiring nuclear imaging data suitable to produce a nuclear tomographic image, said nuclear image data being acquired by a gamma camera head rotating about the subject;

acquiring x-ray imaging data suitable to produce an x-ray tomographic image for attenuation correction of the gamma camera image, said X-ray imaging data being acquired by detectors irradiated by an X-ray source rotating around the subject; and reconstructing an attenuation corrected nuclear medicine image utilizing the nuclear imaging data and x-ray imaging data, said x-ray tomographic image having an RMS noise level of more than about 10 Hounsfield numbers. Preferably, the RMS noise level is more than 15 Hounsfield numbers. Preferably, the RMS noise level is more than 20 Hounsfield numbers. Preferably, the RMS noise level is more than 50 Hounsfield numbers. Preferably, the RMS noise level is more than 100 Hounsfield numbers. In a preferred embodiment of the invention, the RMS noise level is less than about 200 Hounsfield numbers.

In a preferred embodiment of the invention, the x-ray tomographic image has a resolution poorer than about 2 lp/cm in a transaxial direction. Preferably, the resolution is poorer than about 3 lp/cm. Preferably, the resolution is poorer than about 4 lp/cm.

There is also provided in accordance with a preferred embodiment of the invention, a method of producing a nuclear medicine image of a subject, comprising:

acquiring nuclear imaging data suitable to produce a nuclear tomographic image, said nuclear image data being acquired by a gamma camera head rotating about the subject;

acquiring x-ray imaging data suitable to produce an x-ray tomographic image for attenuation correction of the gamma camera image, said X-ray imaging data being acquired by detectors irradiated by an X-ray source rotating around the subject; and reconstructing an attenuation corrected nuclear medicine image utilizing the nuclear imaging data and x-ray imaging data, said x-ray tomographic image having a resolution poorer than about 2 lp/cm. Preferably, the resolution is poorer than about 3 lp/cm. Preferably, the resolution is poorer than about 4 lp/cm.

There is also provided in accordance with a preferred embodiment of the invention, apparatus for producing attenuation corrected nuclear medicine images of patients, comprising:

at least one gamma camera head that acquires nuclear image data suitable to produce a nuclear tomographic image at a first controllable rotation rate about an axis;

at least one X-ray CT imager that acquires X-ray data suitable to produce an attenuation image for correction of the nuclear tomographic image at a second controllable rotation rate about the axis; and a controller that controls the data acquisition and first and second rotation rates to selectively provide at least two of the following seven modes of operation:

(i) an ungated NM imaging mode, in which the first and second rotation rates are the same;

(ii) an ungated NM imaging mode in which the X-ray detectors make a number of rotations and the data from each view of the X-ray acquisition for different rotations is averaged;

(iii) a movement gated NM imaging mode in which the second rotation rate is substantially higher than the first rotation rate and the data from each view of the x-ray acquisition is associated with one of a plurality of respiration gated time periods;

(iv) a respiration gated NM imaging mode in which CT data is acquired over one or a very few rotations while the patient holds his breath, the CT image being used to correct an NM image that corresponds to this condition;

(v) a cardiac gated NM imaging mode in which the second rotation rate is substantially the same as the first rotation rate or in which the second rotation rate is substantially higher than the first rotation rate and the data from each view of the X-ray acquisition for different rotations is averaged, wherein the X-ray data is not correlated with the cardiac cycle;

(vi) a cardiac gated NM imaging mode in which the second rotation rate is higher than the first rotation rate and the X-ray data is binned in accordance with a same binning as the NM data; and (vii) a cardiac gated NM imaging mode in which the X-ray data is which the second rotation rate is substantially the same as the first rotation rate and the X-ray data is binned in accordance with a same binning as the NM data. Preferably, the controller controls the data acquisition and first and second rotation rates to provide at least three of the modes of operation. Preferably, the controller controls the data acquisition and first and second rotation rates to provide at least four of the modes of operation. Preferably, the controller controls the data acquisition and first and second rotation rates to provide at least five of the modes of operation. Preferably, the controller controls the data acquisition and first and second rotation rates to provide at least six of the modes of operation. Preferably, the controller controls the data acquisition and first and second rotation rates to provide all of the modes of operation.

In a preferred embodiment of the invention, the provided modes of operation include at least mode (i). Alternatively or additionally, the provided modes of operation include at least mode (ii). Alternatively or additionally, the provided modes of operation include at least mode (iii). Alternatively or additionally, the provided modes of operation include at least mode (iv). Alternatively or additionally, the provided modes of operation include at least mode (v). Alternatively or additionally, the provided modes of operation include at least mode (vi). Alternatively or additionally, the provided modes of operation include at least mode (vii).

There is also provided in accordance with a preferred embodiment of the invention, a nuclear medicine camera having an X-ray imaging capability, comprising:

at least one gamma camera mounted on a gantry; and an X-ray CT imager mounted on the same gantry, wherein the at least one gamma camera and said X-ray imager are capable of simultaneously rotating about a common axis at different rotation rates. Preferably, the at least one gamma camera and said X-ray imager are capable of simultaneously rotating about a common axis at the same rotation rate.

There is also provided in accordance with a preferred embodiment of the invention, a nuclear medicine camera having an X-ray imaging capability, comprising:

a pair of gamma cameras mounted on a gantry and capable of being rotated together at a common first rotation rate about an axis, said pair of gamma cameras having a controllable angle therebetween and being capable of acquiring nuclear imaging data for reconstructing a tomographic nuclear image; and an X-ray CT imager mounted on the same gantry and being capable of acquiring x-ray imaging data for reconstructing a x-ray image; and a controller that controls the angle between the gamma cameras.

There is also provided in accordance with a preferred embodiment of the invention, a nuclear medicine camera having an X-ray imaging capability, comprising:

at least one gamma camera mounted on a rotor of a gantry and being capable of acquiring nuclear imaging data for reconstructing a nuclear image; and an X-ray CT imager mounted on a rotating portion of the same gantry and being capable of acquiring x-ray imaging data for reconstructing a x-ray image;

image processing circuitry not situated on a rotating portion of the gantry; and a common conduit for transferring said nuclear and X-ray imaging data to said circuitry. Preferably, the camera includes additional image processing circuitry mounted on the rotating portion of the gantry, said additional circuitry providing preliminary processing to at least one of the x-ray and nuclear imaging data prior to said transferring. Alternatively or additionally, the image processing circuitry is used to reconstruct the CT and NM images. Preferably, common circuitry is used to reconstruct the CT and NM images. Preferably, the common circuitry comprises a same CPU.

In a preferred embodiment of the invention, the camera comprises common software used to reconstruct the CT and NM images. Alternatively or additionally, the camera comprises a multiplexer which multiplexes the nuclear and x-ray data prior to said transmission. Preferably, the camera comprises a demultiplexer that demultiplexes the nuclear and x-ray data after said transmission.

In a preferred embodiment of the invention, the common conduit includes slip rings. Alternatively or additionally, the common conduit includes a wireless link.

There is also provided in accordance with a preferred embodiment of the invention, a method of mounting a CT imager on a gantry:

determining a center of rotation of a rotor of the gantry;

siting a plurality of mounting elements at predetermined positions with respect to the center of rotation; and attaching the mounting elements to the rotor while keeping the mounting elements at the predetermined positions. Preferably, the method comprises:

providing a positioning jig referenced to said center of rotation; and attaching said mounting elements on said jig. Preferably, the method comprises:

centering a post at the center of rotation; and mounting said jig on said post.

In a preferred embodiment of the invention, the method comprises:

providing an x-ray source wherein the source is referenced to a first mounting reference thereon;

providing an x-ray detector system wherein the detector is referenced to a second mounting surface thereon; and mounting the x-ray source and x-ray detector on said attached mounting elements. Preferably, the mounting elements comprise alignment elements which mate with matching elements on the first and second mounting references.

In a preferred embodiment of the invention, attaching comprises gluing. Alternatively or additionally, attaching comprises attaching with screws.

There is also provided in accordance with a preferred embodiment of the invention, apparatus for producing attenuation corrected nuclear medicine images of patients, comprising;

a plurality of gamma camera heads that acquire nuclear image data at a plurality of positions about an axis, suitable to produce a nuclear tomographic image;

at least one X-ray CT imager that acquires X-ray data suitable to produce an attenuation image for correction of the nuclear tomographic image at a plurality of positions about and axis;

image processing circuitry that produces attenuation corrected nuclear images utilizing said nuclear and x-ray data; and a controller that controls the data acquisition and image processing circuitry to selectively operate in SPECT mode in which a SPECT image is produced and a PET mode in which a PET image is produced.

There is also provided in accordance with a preferred embodiment of the invention, a method of nuclear imaging, including acquiring attenuation data for correcting the nuclear image, comprising:

acquiring nuclear emission data over a first axially extending portion of the body;

determining an extent of a radioactive region of interest in the body; and acquiring transmission data over a second axially extending portion of the body, responsive to the determined extent. Preferably, the second axially extending portion is smaller than the first axially extending portion. Alternatively or additionally, determining an extent comprises acquiring a planar nuclear emission image. Alternatively or additionally, determining an extent comprises determining said extent from said acquired nuclear emission data.

In a preferred embodiment of the invention, the transmission data is acquired using an x-ray source. Alternatively or additionally, the transmission data is acquired using a gamma ray source.

There is also provided in accordance with a preferred embodiment of the invention, a method of acquiring attenuation data for correcting a nuclear image, comprising:

determining an extent of an organ of interest in the body;

acquiring nuclear emission data over a first axially extending portion of the body larger than the organ of interest; and acquiring transmission data over a second axially extending portion of the body, responsive to the determined extent of the organ, said second portion being substantially smaller than the first portion. Preferably, determining an extent comprises acquiring a planar x-ray image. Alternatively or additionally, the transmission data is acquired using an x-ray source. Alternatively or additionally, determining an extent comprises acquiring a planar transmission gamma ray image. Alternatively or additionally, the transmission data is acquired using a gamma ray source. Alternatively or additionally, determining an extent comprises acquiring a planar nuclear emission image.

In a preferred embodiment of the invention, determining an extent comprises determining said extent from said acquired nuclear emission data There is also provided in accordance with a preferred embodiment of the invention, a method of producing a nuclear medicine image of a subject, comprising:

acquiring nuclear imaging data suitable to produce a nuclear tomographic image, said nuclear image data being acquired by a gamma camera head rotating about the subject;

acquiring x-ray imaging data suitable to produce an x-ray tomographic image for attenuation correction of the gamma camera image, said X-ray imaging data being acquired by detectors irradiated by an X-ray source rotating around the subject;

reducing the sensitivity of gamma camera head while the X-rays are produced; and reconstructing an attenuation corrected nuclear medicine image utilizing the nuclear imaging data and x-ray imaging data. Preferably, the gamma camera head includes a plurality of photomultiplier tubes having dynodes, wherein reducing the sensitivity includes reducing voltages on said dynodes.

There is also provided in accordance with a preferred embodiment of the invention, a method of producing a nuclear medicine image of a subject, comprising:

acquiring nuclear imaging data suitable to produce a nuclear tomographic image, said nuclear image data being acquired by a gamma camera head rotating about the subject;

acquiring x-ray imaging data suitable to produce an x-ray tomographic image for attenuation correction of the gamma camera image, said X-ray imaging data being acquired by detectors irradiated by an X-ray source rotating around the subject for a plurality of rotations;

averaging x-ray imaging data of a same view taken at different rotations of the X-ray source to produce averaged X-ray imaging data;

reconstructing an attenuation corrected nuclear medicine image utilizing the nuclear imaging data and the averaged x-ray imaging data. Preferably, the method includes binning the x-ray data with respect to a physical variable, and wherein said averaging is performed on data in the same bin and having the same view. Alternatively or additionally, the method includes gating the x-ray responsive to a physical variable.

There is also provided in accordance with a preferred embodiment of the invention, apparatus for producing attenuation corrected nuclear medicine images of patients, comprising;

a plurality of gamma camera heads that acquire nuclear image data suitable to produce a nuclear tomographic image at a plurality of positions about an axis;

at least one X-ray CT imager that acquires X-ray data suitable to produce an attenuation image for correction of the nuclear tomographic image at a plurality of positions about and axis, said X-ray CT imager comprising a stationary anode X-ray tube.

There is also provided in accordance with a preferred embodiment of the invention, a registration phantom for registering transmission and emission imaging systems, comprising:

a substantially attenuating phantom body formed with a plurality of cavities; and radio-emissive material filling the cavities. Preferably, at least one of the cavities is a long thin cavity. Alternatively or additionally, at least one of the cavities is a spherical cavity. Alternatively or additionally, the phantom includes a plurality of radio-opaque marking elements axially offset from said cavities.

In a preferred embodiment of the invention, the phantom includes at least three such cavities. Preferably, the phantom includes at least four such cavities. Preferably, the phantom includes at least six said cavities.

There is also provided in accordance with a preferred embodiment of the invention, a method of determining a coordinate transformation between a nuclear emission imaging system and a transmission imaging system comprising:

providing a phantom having elements that are imageable by said nuclear emission imaging system and elements imageable by said transmission imaging system;

imaging said phantom by both said systems to provide emission and transmission images of the phantom; and determining the transformation from a comparison of said emission and transmission images. Preferably, the transmission images are X-ray images. Alternatively or additionally, the transmission images are gamma ray images.

In a preferred embodiment of the invention, the phantom comprises:

a phantom body formed with a plurality of cavities; and radio-emissive material filling the cavities. Preferably, the phantom comprises a plurality of radio-opaque marking elements axially offset from said cavities. Alternatively or additionally, at least one of the cavities is a long thin cavity. Alternatively or additionally, at least one of the cavities is a spherical cavity.

In a preferred embodiment of the invention, the radio-emissive material is radio-opaque.

BRIEF DESCRIPTION OF THE DRAWINGS

The present invention will be more clearly understood from the following description of the preferred embodiments thereof, taken together with the following drawings, in which.

DETAILED DESCRIPTION OF PREFERRED EMBODIMENTS OF THE INVENTION

Figure 1B:
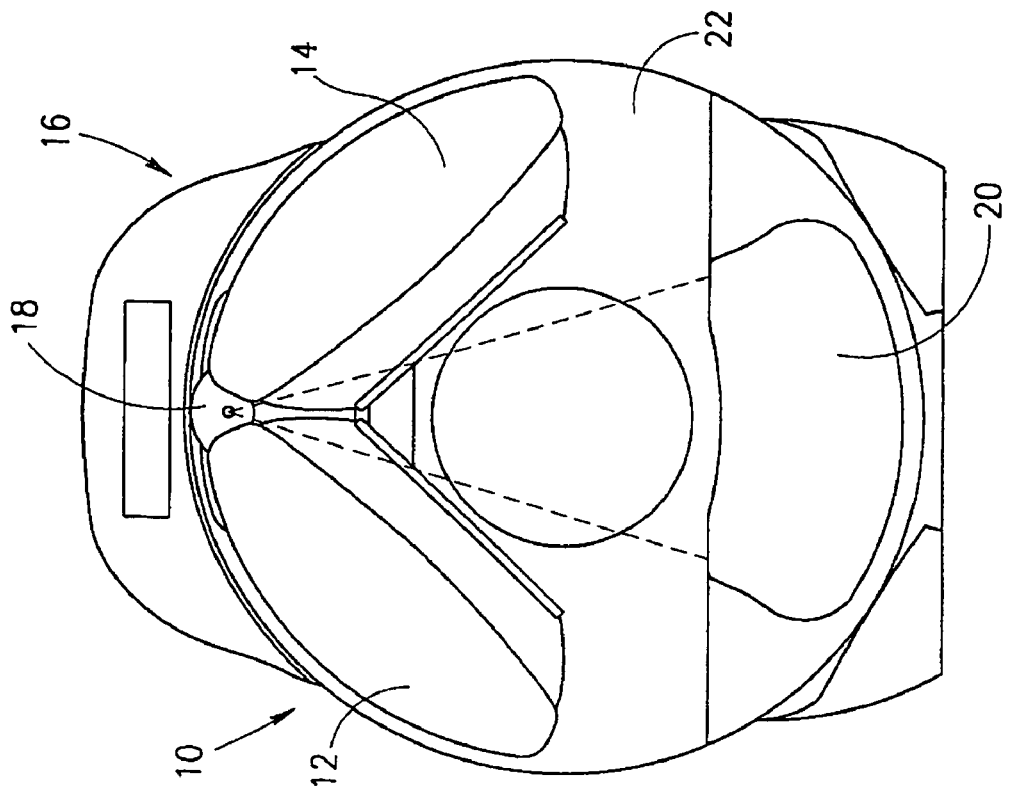
FIGS. 1A and 1B are end views of a gamma camera system with attenuation correction, in accordance with a preferred embodiment of the invention.
Figure 1A:
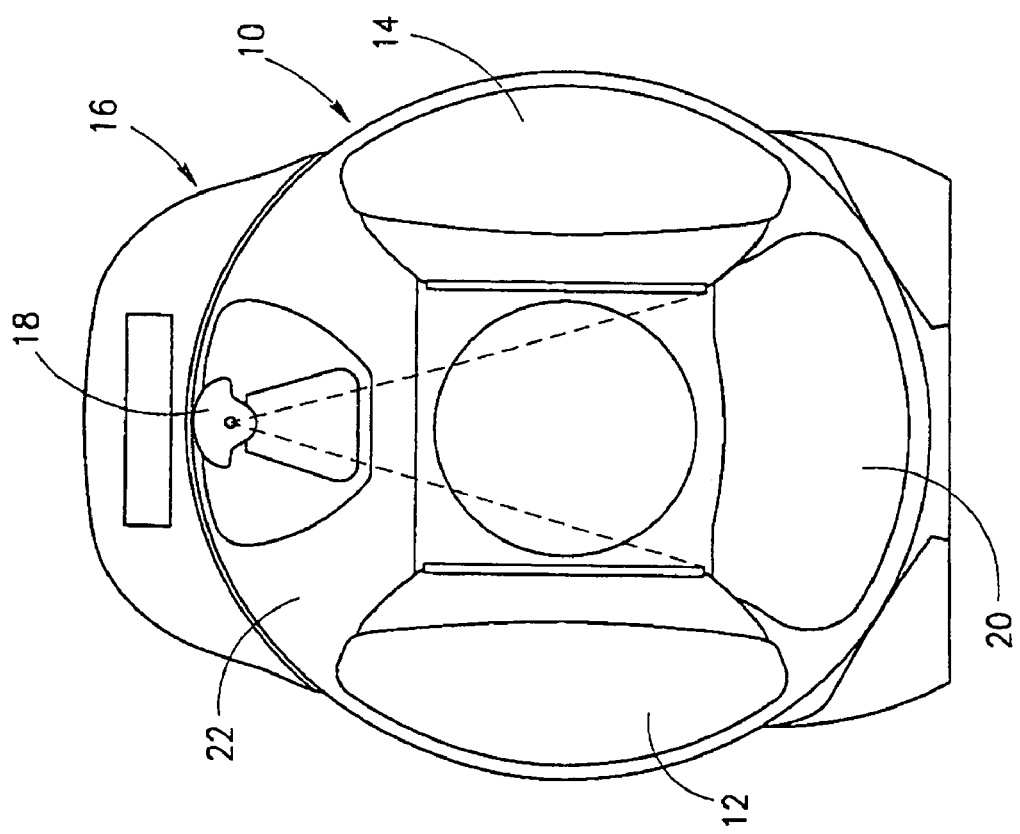
Figure 1C:
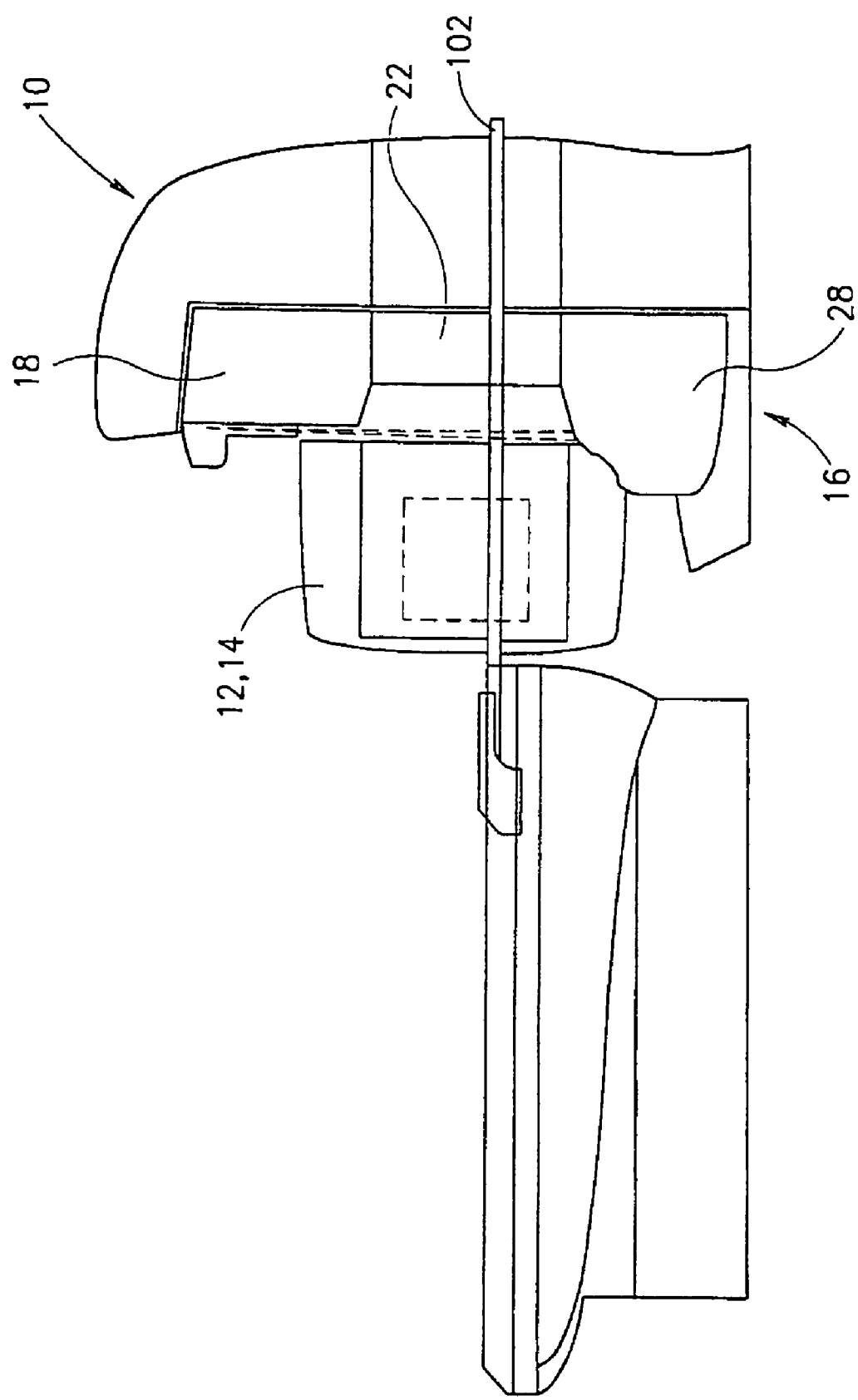
FIG. 1C is a side view of the gamma camera system of FIGS. 1A and 1B.

FIGS. 1A and 1B illustrate end views and FIG. 1C illustrates a lateral view of a gamma camera system 10, with attenuation correction, in accordance with a preferred embodiment of the invention. Camera system 10 preferably comprises a pair of gamma camera heads 12 and 14 and an X-ray imaging system 16. System 16 preferably comprises an X-ray source 18 and a plurality of X-ray detectors arranged in an array 20. Camera heads 12 and 14 and system 16 are preferably mounted on a same gantry 22, as shown in FIGS. 1A–1C. However, for some preferred embodiments of the invention (which may not embody all the above mentioned aspects of the invention) the camera heads and the X-ray system are mounted on different gantries. For some preferred embodiments of the invention, only a single gamma camera head is required. In others three or four heads, equally spaced circumferentially about the axis of rotation are used.

A patient (not shown in FIGS. 1A–1C) is preferably placed on a table 102 which is advanced along an axis of rotation of camera heads 12 and 14 and system 16. A radio-isotope is selectively situated inside the patient, by conventional means such as via the blood stream (intravenous injection) or the lungs (inhalation) or by other means known in the art. Preferably, heads 12 and 14 generate nuclear imaging data signals in response to gamma rays generated by the radioisotopes.

Similarly, X-ray source 18 irradiates the patient, and array 20 generates X-ray data signals, in response to X-rays from source 18 which impinge on the X-ray detectors, after passing through the patient.

As shown in FIGS. 1A and 1B, the angle between heads 12 and 14 is preferably adjustable between 90 degrees and 180 degrees, using conventional means. Furthermore, the distance between the heads may be adjusted and the transverse positions of each of the heads (or of both together) may be adjusted, using conventional mechanical structures. Alternatively, the heads are fixed at one of the positions of FIGS. 1A and 1B. Further alternatively, three gamma cameras may be provided, namely the two shown in FIG. 1B plus a third camera, below and between the two cameras shown.

Figure 1D:
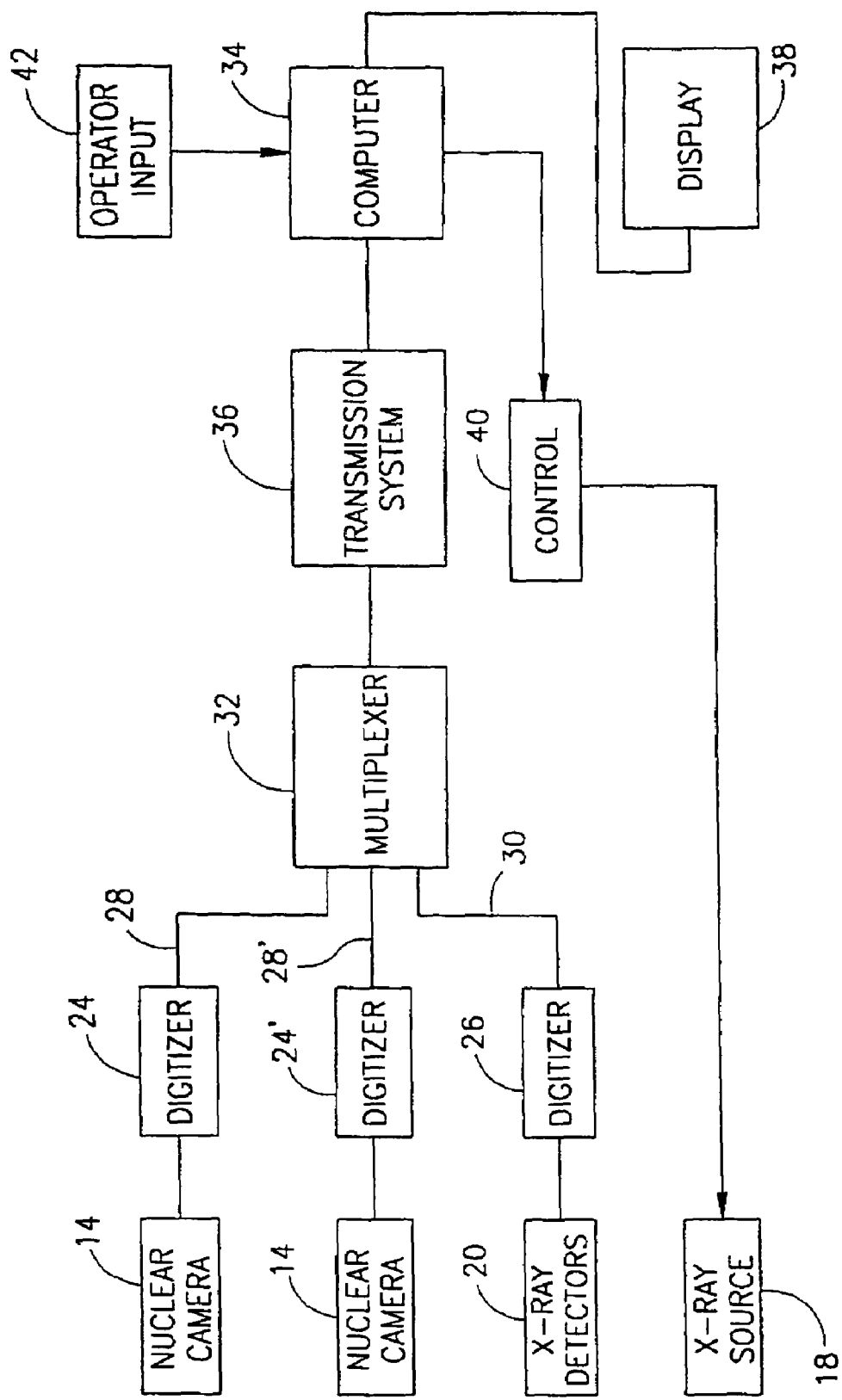
FIG. 1D schematically shows circuitry for information transfer, control and image reconstruction, for the system of FIGS. 1A–1C.

Referring additionally to FIG. 1D, in a preferred embodiment of the invention, the nuclear energy signals and the X-ray signals are digitized in digitizers 24 (and 24') and 26, respectively to produce digital signals on lines 28 and 30 respectively. Digitizing by digitizers 24 and 26 may be preceded by some signal processing and/or image pre-processing, as known in the art. In a preferred embodiment of the invention, the signals on lines 26 and 28 are multiplexed (and optionally compressed) by a multiplexer 32 and fed to a computer 34 via a transmission system 36. Alternatively, one or both of the x-ray and emission data (SPECT/PET) are preprocessed in corresponding hardware/software and then fed into multiplexer 32. It should be understood that in most of the embodiments shown herein PET or SPECT imaging may be performed. In preferred embodiments of the invention, the NM imaging mode may be switched between PET and SPECT.

In computer 34, the signals are de-multiplexed (and if necessary, decompressed) for processing (utilizing algorithms known in the art) to produce three dimensional (or two dimensional slice) images. These images which may be displayed on a display 38, stored in a memory in the computer, or both. Preferably, the nuclear images are corrected for attenuation of intervening tissue and bones, three-dimensional attenuation images produced from data generated from the transmission (X-ray) signals. Such correction may use any of the algorithms known in the art.

In general, the nuclear medicine data may include raw data (the outputs of photomultiplier tubes or pixelized detectors of the camera heads) or calculated positions of detected nuclear events on the heads (either uncorrected positions or positions corrected for camera head distortions). In producing the nuclear image and the transmission (attenuation) image, the (angular) position of the camera heads and the x-ray system and the lineal position of the table with respect to the heads and x-ray system are taken into account by computer 34. These positions are preferably measured by transducers or encoders or by other means, as known in the art.

In a preferred embodiment of the invention, the same CPU and/or other hardware infrastructure is used in generating both the nuclear medicine image and the attenuation image used to correct it. Alternatively or additionally, the same software is used to generate the three dimensional nuclear medicine and attenuation images. In general, the reconstruction algorithms used for X-ray CT reconstruction and SPECT reconstruction are the same or very similar. Some types of PET reconstruction also use some of the same algorithms used for CT reconstruction. In general, use of the same hardware, and to some extent, of the same software, allows for a less expensive overall system cost. Of course, achieving these advantages does not necessarily require that the data be multiplexed and transmitted over the same line or transmission channel, as described above.

However, in a preferred embodiment of the invention, digitizers 24 and 26, lines 28 and 30 and multiplexer 32 are mounted on the moving portion of gantry 30. Thus, if only a single transmission system 36 is required, there is a considerable saving in system complexity and cost. In a preferred embodiment of the invention, transmission system 36 comprises a slip ring system. In an alternate preferred embodiment of the invention, the transmission system comprises a radio or optical link. Alternatively, the transmission system comprises a coiled transmission line which unwinds as the camera heads rotate. In any event, the use of a single link greatly simplifies the transmission of data to the computer and reduces the complexity of the transmission system.

In a preferred embodiment of the invention, the nuclear imaging signals and the x-ray signals are preferably acquired over different extents of the patient. In a preferred embodiment of the invention, transmission data is acquired only for axial slices for which significant nuclear activity is indicated or may be expected. For other slices, no attenuation correction data is acquired and the nuclear image is not corrected for attenuation. This more limited acquisition of transmission data means that the patient is irradiated by the X-rays for a shorter time and over a smaller portion of his body.

The portion of the patient's body over which transmission data should be acquired may be determined in a number of ways. For example, a low energy, one dimensional transmission X-ray "scout" image may be acquired to locate the position of an organ of interest. The scout image is preferably "assembled" by computer 34 and displayed on display 38. In a preferred embodiment of the invention, an operator indicates the extent of the organ, on the image, to computer 34. A controller 40, receives commands from computer 34 and activates X-ray source 14, responsive to the commands, only for those axial positions for which radiation is necessary to correct for attenuation. The patient is irradiated with X-rays only over the axial extent of the organ or other region of interest.

Alternatively or additionally, the uncorrected nuclear image or a planar nuclear image is acquired first and displayed. The extent of region of nuclear activity is determined, either by the operator, or automatically by the computer. A transmission image is then acquired as indicated above, only for this axial region.

Alternatively, the nuclear data is analyzed for nuclear activity, on a slice by slice basis, to determine if transmission data is to be acquired.

It should be noted that while in a preferred embodiment of the invention, an X-ray transmission system is utilized, the advantages of reduced transmission radiation exposure can also be achieved when a radionuclide source is used for transmission imaging. Preferably, a shutter is used to cover the radio nuclide source when transmission imaging data is not required.

Alternatively or additionally, in a preferred embodiment of the invention, the X-ray energy used to irradiate the patient is further reduced by reducing the quality requirements for the X-ray CT transmission image below that normally required for such images. In general, CT images are acquired at a relatively high X-ray energy in order to allow for the reconstruction of high quality attenuation images. However, attenuation images utilized for correction of nuclear medicine images may be degraded to match the image quality levels (spatial resolution, signal to noise and other such factors) of the nuclear image. Thus, while normal CT imaging utilizes X-ray levels suitable for 10–20 lp/cm resolutions, for attenuation corrections, a spatial resolution of 1–3 or even 4 lp/cm is sufficient. Additionally, while an RMS noise level of 1–5 Hounsfield numbers is generally considered to be required for CT imaging, CT imaging for attenuation correction requires only a noise level of about 10, 20, 50, 100 or even 200 Hounsfield numbers. This results in an X-ray system having much lower energy and power requirements than those of "standard" CT systems and a much lower weight. Importantly, the amount of radiation to which the patient is exposed from the transmission source is greatly reduced. Furthermore, the alignment accuracy required for the CT system is also reduced, since the accuracy of alignment required is reduced in proportion to the reduced resolution. These reduced requirements allow for the mounting of an appropriate CT system on a nuclear medicine gantry, without the normal strict mechanical requirements for a CT system.

It should be noted that as used herein the term "energy" means "power times time" and not photon energy.

A further reduction of weight can be achieved by reducing the power required in addition to the total energy required. In particular, while CT imaging is generally performed at a rotation rate of up to 2 Hz, CT imaging for attenuation correction can be performed (in some circumstances, as described below) at rotation rates compatible with those utilized for the acquisition of nuclear imaging data. These rotation rates may be as fast as 3 cycles per minute, but are generally slower that that. Thus, normal X-ray CT rotation rates are more than an order of magnitude faster than normal NM rotation rates and those used in preferred embodiments of the present invention.

The reduction in energy can be achieved in one of a number of ways. One way is to reduce the power of the CT. This may be advantageous even if the total energy is not reduced, since it can result in a lower cost and weight X-ray system (for example, using a fixed anode tube and/or using a smaller power supply, preferably mounted on the rotor of the gantry (to avoid transfer of high voltages to a moving rotor).

One way of reducing the power is to use a less powerful X-ray source. This can reduce the weight and cost of the system substantially. A lower cost stationary anode X-ray tube can be used. Alternatively or additionally, the power supply for the tube mounted on and preferably integrated with the tube on the rotor. This allows for transfer of line voltage, rather than high voltage, to the rotor for the X-ray supply. Alternatively, a higher power tube may be used and the tube pulsed for only a short time (low duty cycle). This pulsing can take place for example when the X-ray system is in a position in which data should be acquired. This can also allow for a system with the same or similar benefits.

In a preferred embodiment of the invention, the relative speeds of rotation of the nuclear and X-ray imaging systems are controlled and optimized to provide improved images, depending on the type of image being acquired. In particular, a system in accordance with this embodiment is capable of operating in one or more of the following modes:

1) An ungated NM imaging mode, in which the X-ray detectors rotate together with the NM detectors or in which the X-ray detectors make a number of rotations and the data from the same view for different rotations is averaged.

2) A respiration gated NM imaging mode in which the CT data is acquired in a high rotation rate mode, and the data from each view is associated with one of the respiration gated time periods. In this mode, unaveraged CT data may be used to generate a higher resolution, if noisier image.

3) A respiration gated NM imaging mode in which CT data is acquired over one or a very few rotations while the patient holds his breath. The CT image is then used to correct an NM image that corresponds to this (breath holding) condition.

4) A cardiac gated NM imaging mode in which the CT data is acquired either in a slow rotation rate mode or in a fast rotation rate mode with averaging of the data to simulate slow rotation. In this mode, the attenuation data is not correlated with the cardiac cycle. However, the CT image is based on averaged data over the cardiac cycle.

5) A cardiac gated NM imaging mode in which the CT data is acquired in a fast rotation rate mode with gating of the CT data in accordance with the same or similar binning as the NM data.

In a preferred embodiment of the invention, computer 34 is supplied with a user input 42. A user may choose from one of a series of protocols, which may have one or more of the above rotation rate relationships.

In one preferred embodiment of the invention, the nuclear medicine and x-ray systems are mounted on a single rotating element and thus, rotate together. For such systems, acquisition of X-ray and Nuclear Medicine image data at different rotation rates (as is common in the art) requires that the nuclear medicine system be rotated at a much higher rate than is usual for such systems. In addition to subjecting the gamma camera heads to undue stress, this requires a much heavier and more expensive gantry.

Therefore, in a preferred embodiment of the invention, means are provided for rotating the two imaging systems independently. In one preferred embodiment of the invention, the two imaging systems are mounted on separate gantries, as in the above referenced U.S. Pat. No. 5,391,877. In others, a single gantry is provided. However, a plurality of different concentric bearings are provided. One of these allows for the rotation of one of the imaging systems with respect to the fixed reference while the other allows for the rotation of the second imaging system with respect to the first imaging system. This may be achieved, for example, by mounting the gamma cameras on an outer ring which rotates, on bearings, mounted in a fixed portion of the gantry. The X-ray system is mounted on a second ring which rotates on bearings mounted on the outer ring. The rings are driven by separate motors. This construction assures that the two systems rotate about a common axis, which aids in alignment and correlating of the imaging systems.

In a preferred embodiment of the invention, a single power line is used to supply all of the equipment which rotates. As shown in FIG. 1D, controller 40 activates the X-ray system when transmission data is required. In addition, controller 40 may be used to distribute power to the X-ray detector electronics, and the gamma camera heads. This use of a single power line for the moving portions of the gantry results in reduced system complexity and costs. The line power may be transferred utilizing, for example, slip rings. Alternatively, it may be transferred utilizing a rolled up cable, which unwinds as the heads and X-ray system rotates. Controller 40, whose function may be distributed over a number of controllers, is preferably situated on the moving portion and preferably receives its commands via the same multiplexed transmission link, described above, used for data transfer.

In a preferred embodiment of the invention, the Nuclear medicine system can be operated in one of several modes:

1) PET—The nuclear detectors are preferably fitted with one or two dimensional widely spaced septa to block large angle coincidence events. Alternatively no septa are used. Coincidence events are acquired over one or more rotations of detectors 12 and 14.

2) SPECT—The nuclear detectors are fitted with Multichannel collimators to detect gamma radiation. The detectors may be used singly, or together at 90 or 180 degree apart configurations. A series of views are taken about at least 180 degrees of the patient. (Only 90 degrees of rotation of the gantry is required for the 90 degree detector configuration.) In each view detectors 12 and 14 can be moved close to the patient to improve resolution of the images.

3) Whole Body—In each of PET and SPECT as described above, the detectors image a large axial distance of 400–500 mm. Larger areas can be covered by translating the patient axially. This axial translation may be performed in steps, between rotations of detectors 12 and 14, or continuously while rotating the detectors, in a spiral mode.

In each of the above modes, the NM data can be complemented with X-ray attenuation data derived from X-ray transmission imaging. The X-ray images may be acquired before, during or after the SPECT or PET images. As indicated above, the X-ray images may be acquired over only a part of the axial length of the scan and may be acquired in a step and shoot or helix mode.

Emission and transmission scans may be interlaced with each other or the emission sequences may all be taken together. For longer scans, simultaneous transmission and emission imaging may take place over different portions of the body.

In a preferred embodiment of the invention the photomultiplier tubes (PMTs) are turned off or their sensitivity is reduced while the X-ray is on. This is desirable, since the x-ray flux is very high and can saturate and blind the PMTs. One possible methodology is to turn off the PMTs completely. However, if the PMTs are turned off, the cameras take a substantial time to stabilize after they are turned on again. In a preferred embodiment of the invention, the PMT dynode voltages are reduced, thus substantially reducing the gain of the PMTs and avoiding blinding and damage to the PMTs. Additionally or alternatively, an x-ray filter may be placed over the detector. However, due to the high flux of x-rays, this is often not sufficient by itself.

The alignment and mounting of an X-ray CT imaging system in accordance with a preferred embodiment of the invention, is illustrated with reference to FIGS. 2–8.

Figure 2:
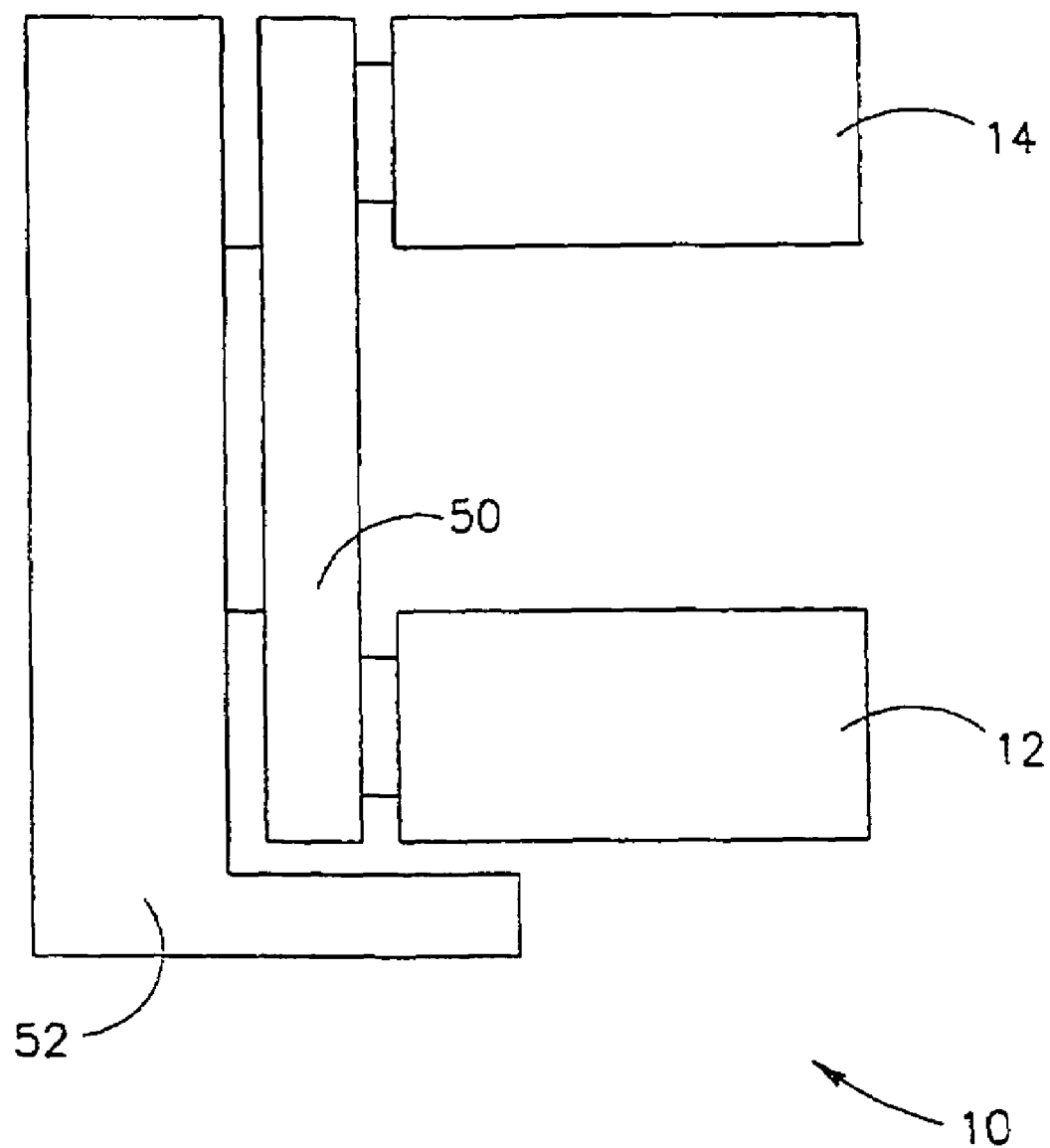
FIG. 2–8 illustrate the alignment of an X-ray CT imaging system in accordance with a preferred embodiment of the invention.

FIG. 2 shows a system 10 prior to the mounting of the X-ray system. As illustrated, the gamma camera heads are already mounted; however, the gamma camera heads, whose alignment is not critical, may be mounted after the mounting of the X-ray system. On FIG. 2, the rotating portion (rotor) of the gantry (on which the X-ray system is to be mounted) is indicated by reference 50 and the stationary portion (stator) of the system is indicated by reference 52.

Figure 3:
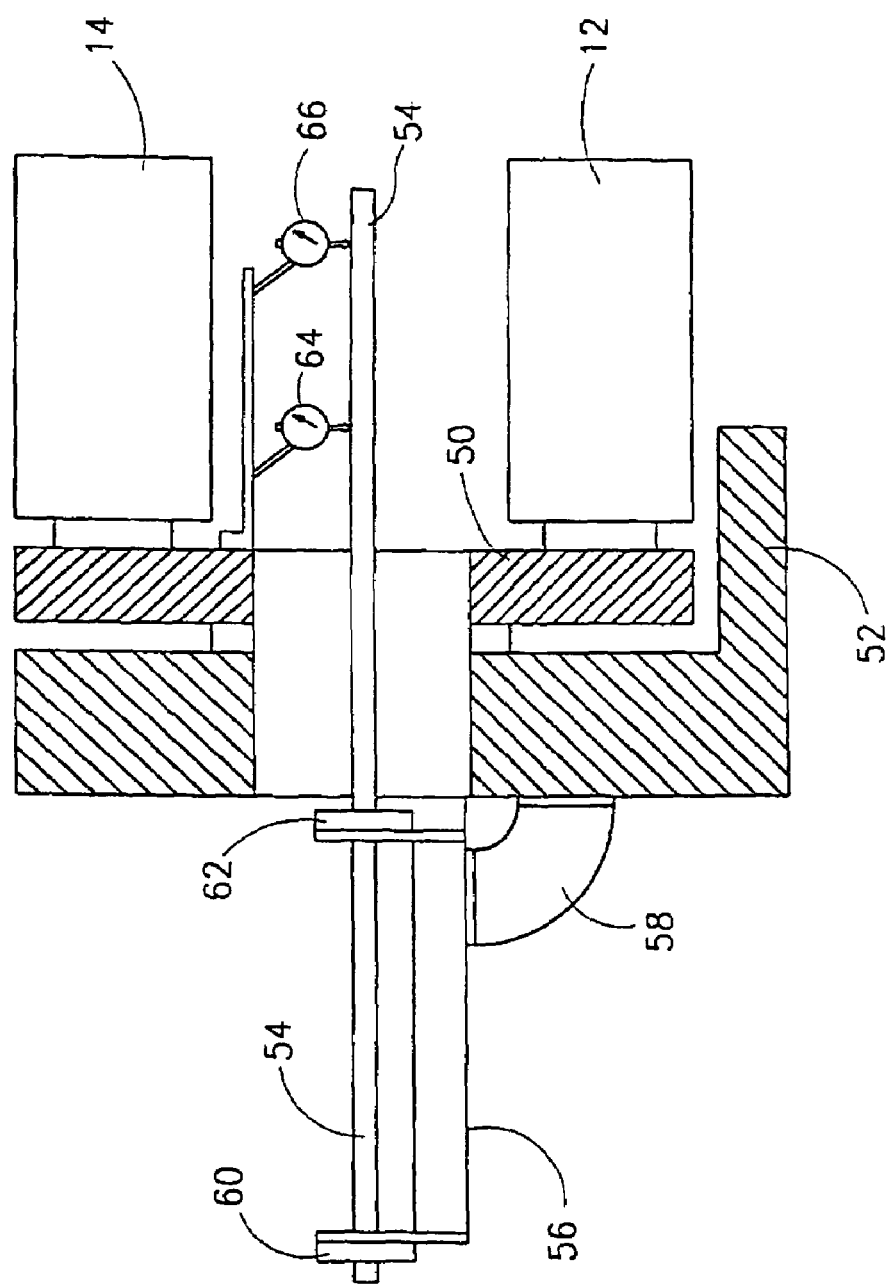

The first stage of the alignment process, illustrated in FIG. 3, is the establishment of a reference to the center of rotation of the gantry. As is well known, accuracy of a CT imaging system depends on an accurate placement of the X-ray source and detectors with respect to the axis of rotation.

A rod 54 is mounted on a rod adjustment device 56, firmly attached to a fixed reference. For example, rod adjustment device 56 may be attached via a bracket 58 to stator 52. Rod adjustment device comprises two spaced apart independent x-y transverse translation mechanisms 60 and 62, to which rod 54 is attached. Two indicators 64 and 66 are mounted on and rotated rotor 50. Translation mechanisms 60 and 62 are adjusted as the rotor is rotated, until rod 54 is centered. Separate adjustment of x and y centering may be necessary. After the rod is centered, the indicators and the bracket on which they are mounted are removed.

Figure 4:
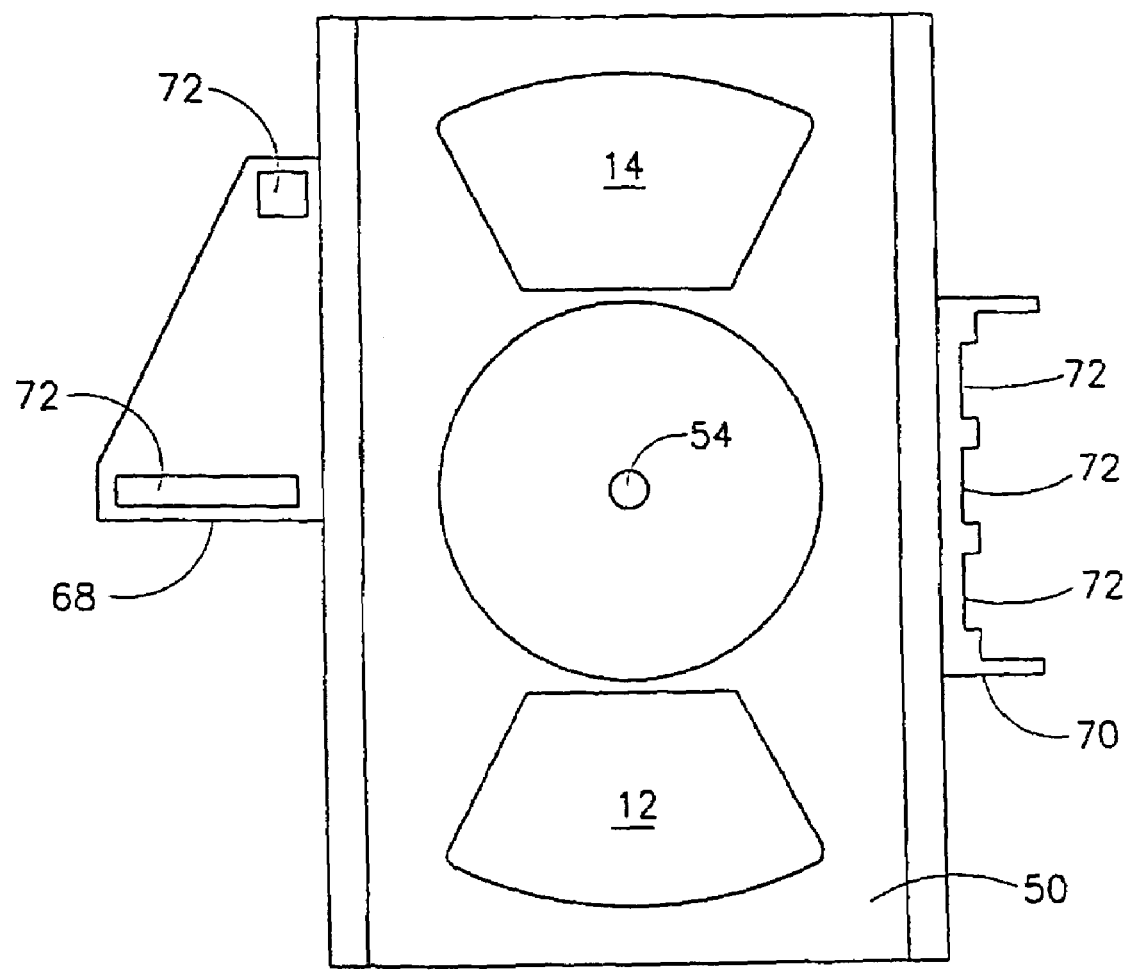

FIG. 4 shows an end view of system 10, after the adjustment of the centering of rod 54. Rod adjustment device 56 continues to hold rod 54 although it is not shown in FIG. 4. An X-ray detector support 68 and an X-ray source support 70 are mounted on rotor 50. The positioning of supports 68 and 70 are each formed with a plurality of glue pockets 72.

Figure 5:
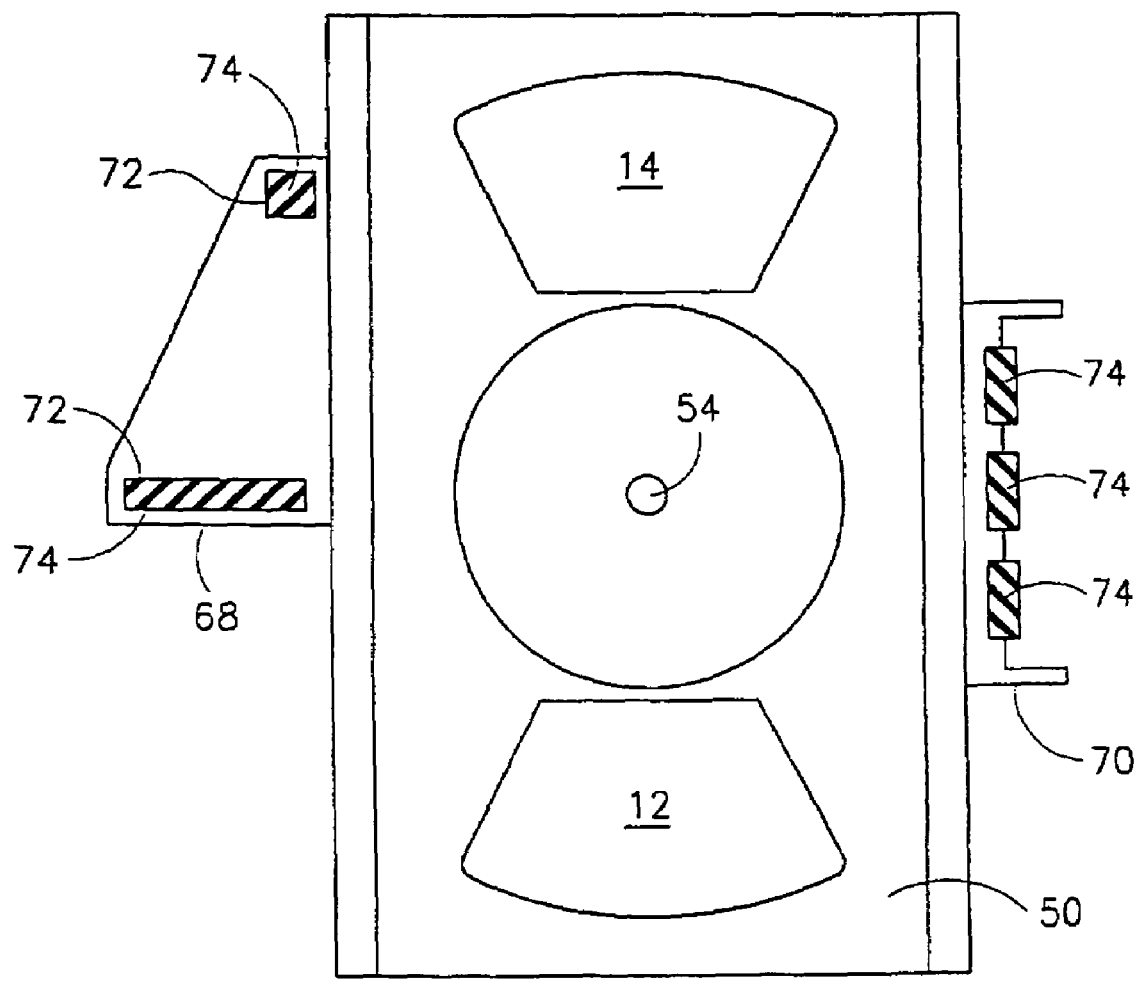

These pockets are filled with glue (for example a high strength epoxy) indicated by reference 74 on FIG. 5.

Figure 6:
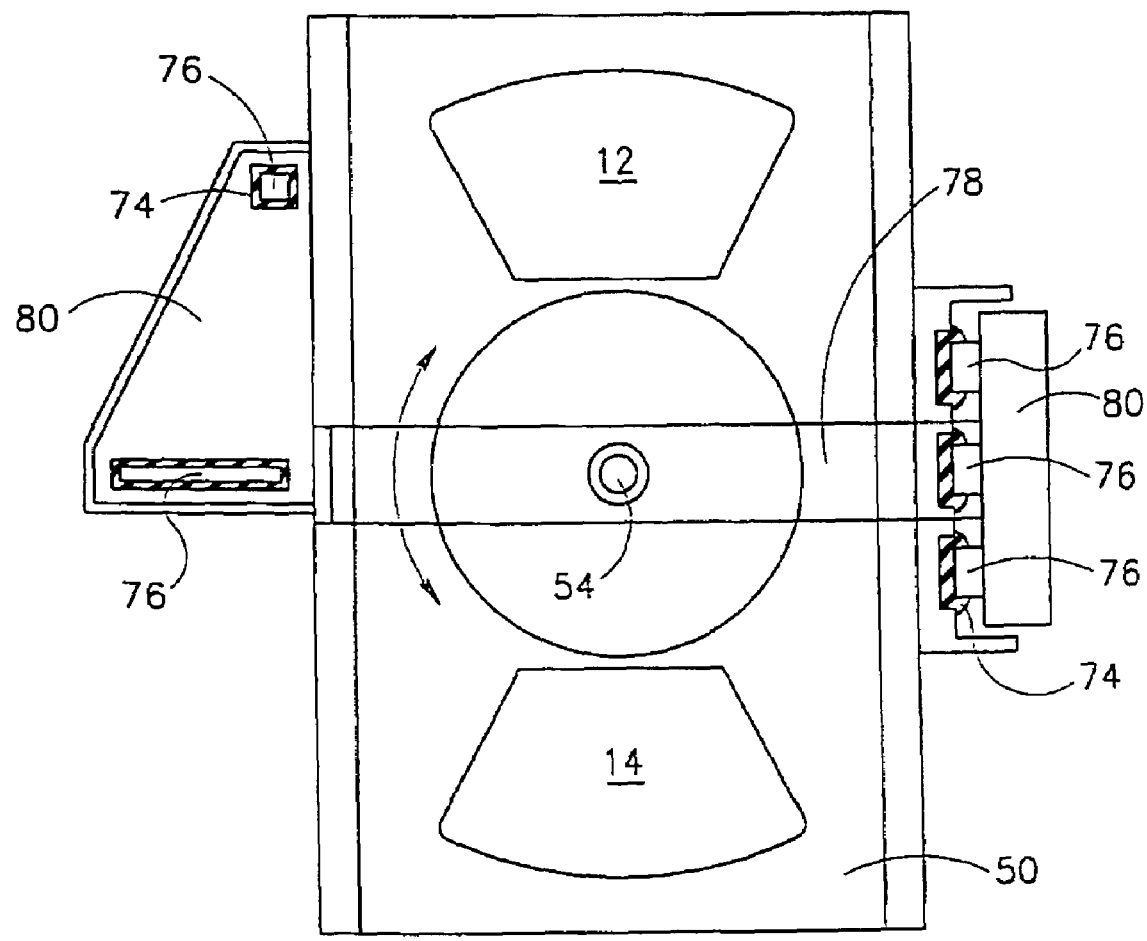

FIG. 6 shows the mounting of a plurality of mounting inserts 76 on supports 68 and 70. In accordance with a preferred embodiment of the invention, as described below, X-ray source 18 and array 20 are mounted on the mounting inserts 76. The step illustrated in FIG. 6 assures that inserts 76 are aligned with the center of rotation of the system, by reference to rod 54.

A bridge 78, is mounted on rod 54. Bridge 78 has a center hole whose size closely matches the diameter of rod 54. Insert holders 80 are mounted on bridge 78 and support inserts 76 in an accurate position vis-à-vis rod 54. While the means for mounting inserts 76 on holders 80 are not shown, they typically include screws for mounting and pins for alignment of the inserts on the insert holders. The bridge is rotated until it is substantially perpendicular to a line connecting the centers of detectors 12 and 14. This adjustment is not critical and may be performed by eye. in addition, the bridge is moved axially along rod 54 until the inserts are approximately centered in pockets 72. This adjustment is not critical either.

The glue is allowed to set and harden. When the glue has hardened sufficiently, bridge 78 and holder are dismantled from rod 54 and inserts 76 leaving the inserts attached to rotor 50 by glue 74. However, due to the method of attachment, the inserts are aligned with rod 54 and hence the center of rotation of rotor 50.

Figure 7:
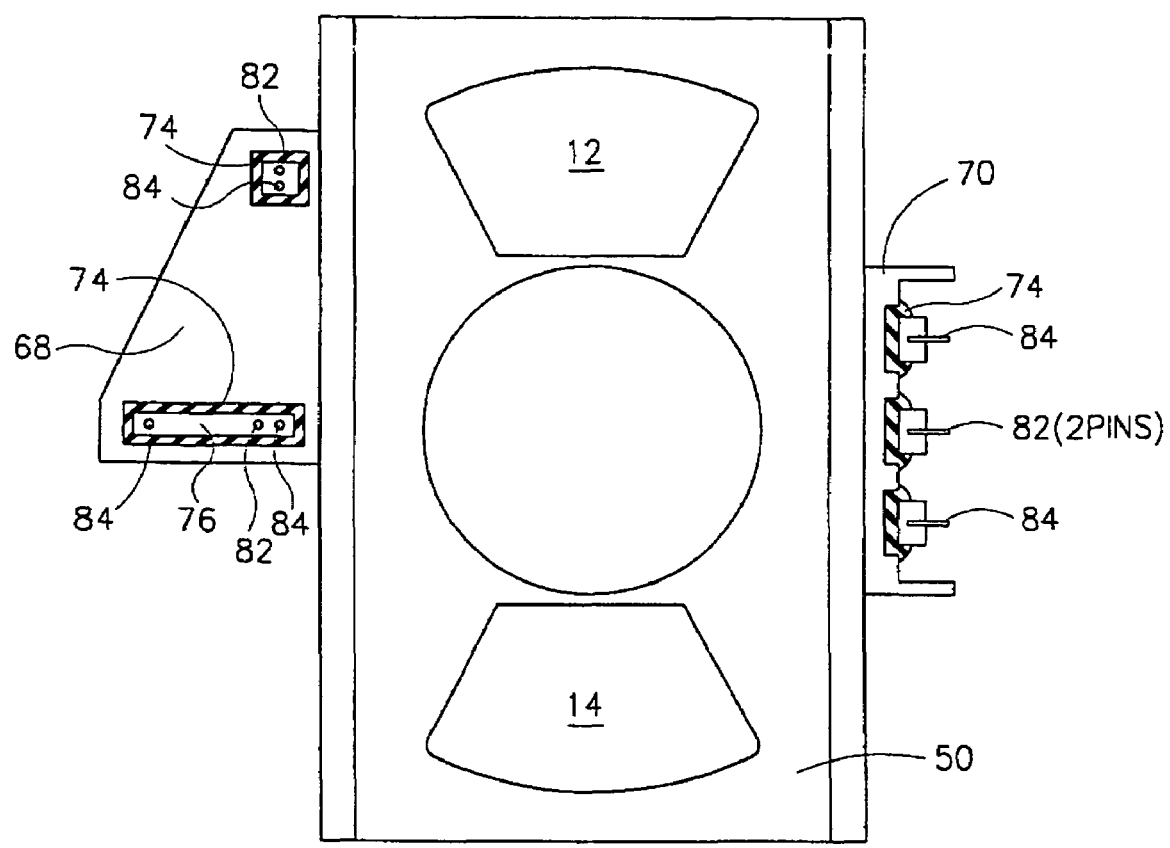

FIG. 7 shows inserts 76 mounted on supports 68 and 70. Inserts 76 comprise a plurality of pins 82 and threads 84 for mounting detector array 20 and X-ray source 18. While a particular arrangement of pins and threads is shown in FIG. 7, any arrangement of pins and threads which provides positive positioning and firm mounting may be used.

Figure 8:
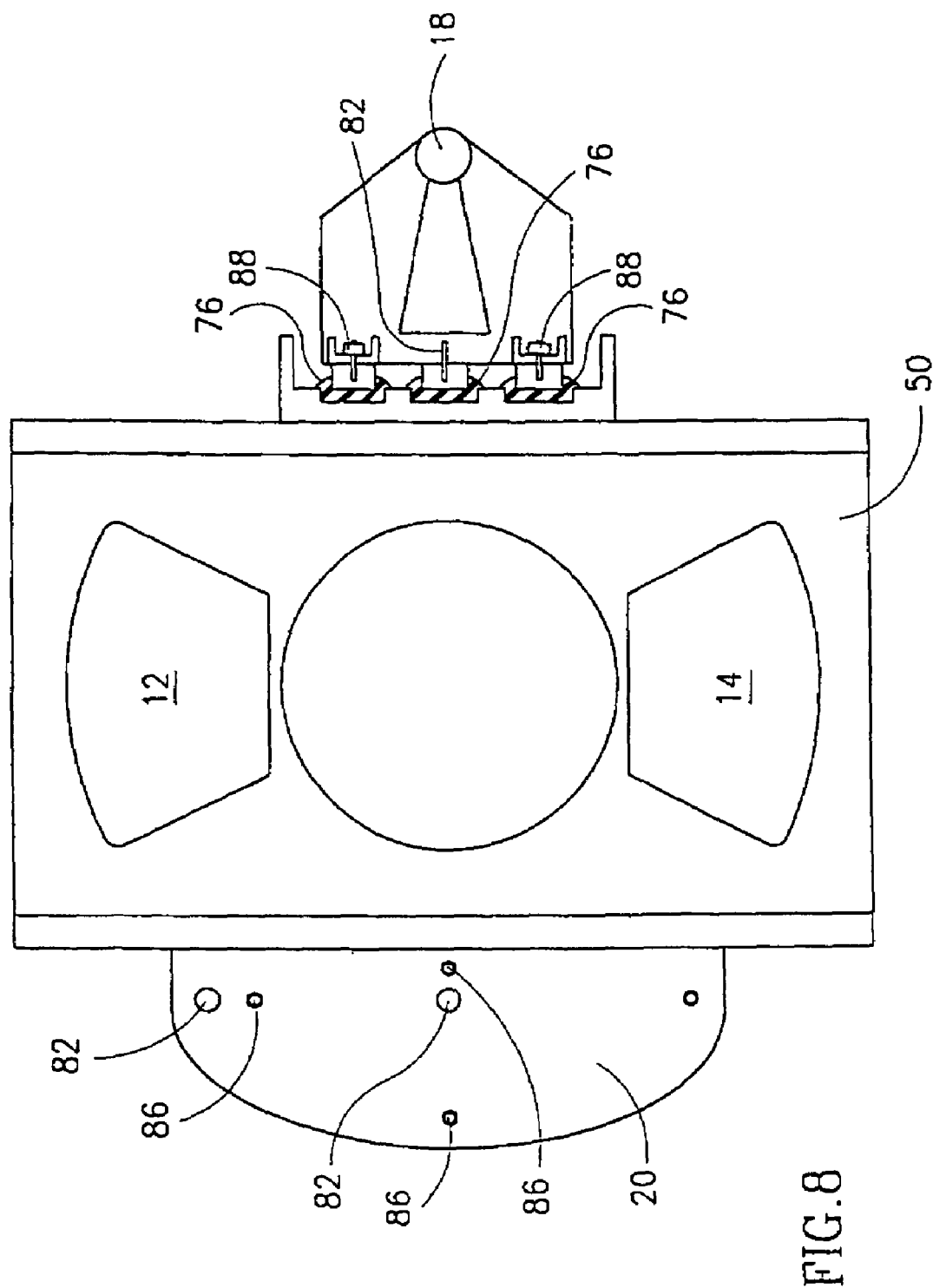

FIG. 8 shows X-ray source 18 and detector array 20 after mounting. X-ray source 18 and detector array 20 are and mounted to inserts 76 by holding screws 86 and holding nuts 88. Pins 82 fit into matching holes in the housings of source 18 and detector array 20. The position and orientation of the X-ray tube and the detectors are closely aligned, in the factory with these holes, such that no additional alignment of the x-ray source and detector array is necessary.

The resulting standardization of positions and alignments allows for the simple field replacement of X-ray source and/or detectors when such replacement is necessary.

In a preferred embodiment of the invention, the relative positions of the coordinate systems of the nuclear medicine imaging system and the X-ray imaging system is determined by imaging a combined X-ray/NM phantom with both systems. A transformation is determined between the coordinate systems, based on a known relationship between NM and X-ray features in the phantom. A suitable phantom is formed with a plurality of cavities or other elements containing radioactive material. Such elements are imaged by both the CT and NM systems. Preferably, the radioactive material is opaque to x-rays. At least three such elements, preferably situated in an axial plane, are usually sufficient to align the system. Preferably 4–6 elements are provided to allow for averaging and for correction of axial skew. In a preferred embodiment of the invention, the cavities are spherical. Alternatively or additionally, at least some of the cavities are thin long cavities. Alternatively or additionally, separate elements, having known positional relationship are used for determining the transformation. Alternatively or additionally, the phantom includes a plurality of radio-opaque marking elements axially offset from said cavities.

In practice, the registration information is used to control combined CT/NM protocols in which the positions of the patient (bed) are automatically controlled for the two acquisitions.

While the gluing system described above is preferred for attaching inserts 76, more conventional positioning with shims or the like may be used, for some preferred embodiments of the invention.

In some preferred embodiments of the invention, the opening for the patient is smaller than in normal X-ray CT devices. Preferably, an arm support device (a frame that limits the radial extent of the patient by folding his arms within the frame) is provided.

The CT system as disclosed may be a single slice CT or a multi-slice CT, in which a plurality of rows of detectors allow for the acquisition of multiple slices of CT data at one time. Alternatively, a large array of detectors may be provided, and a cone beam of X-ray may by used to image a field of view that is similar to or the same as that of the NM detectors.

The present invention has been described using non-limiting detailed descriptions of preferred embodiments thereof that are provided by way of example and are not intended to limit the scope of the invention. Variations of embodiments described will occur to persons of the art. In addition, while preferred embodiments of the invention have been described as having certain groups of features, some preferred embodiments of the invention may include fewer of more of the features or other combinations of features. Furthermore, the terms "comprise," include," and "have" or their conjugates shall mean: "including but not necessarily limited to." The scope of the invention is limited only by the following claims:

The invention claimed is:

1. A method of mounting a CT imager on a gantry;
determining a center of rotation of a rotor of the gantry;
siting a plurality of mounting elements at predetermined positions with respect to the center of rotation;
attaching the mounting elements to the rotor while keeping the mounting elements at the predetermined positions;
providing a positioning jig referenced to said center of rotation; and
attaching said mounting elements on said jig.

2. A method according to claim 1 wherein said method comprises:
centering a post at the center of rotation; and
mounting said jig on said post.

3. A method according to claim 1 and including:
providing an X-ray source wherein the source is referenced to a first mounting reference thereon;
providing an X-ray detector system wherein the detector is referenced to a second mounting reference thereon; and
mounting the X-ray source and X-ray detector on said attached mounting elements.

4. A method according to claim 3 wherein the mounting elements comprise alignment elements which mate with matching elements on the first and second mounting references.

5. A method according to claim 4 wherein attaching comprises gluing.

6. A method according to claim 4 wherein attaching comprises attaching with screws.

7. A method according to claim 3 wherein attaching comprises gluing.

8. A method according to claim 3 wherein attaching comprises attaching with screws.

9. A method according to claim 1 wherein attaching comprises gluing.

10. A method according to claim 1 wherein attaching comprises attaching with screws.

11. A method according to claim 1 further comprising mounting at least one gamma camera on said rotor.

12. A method according to claim 11 further comprising providing said gantry with a stationary portion.

13. A method according to claim 12 wherein mounting at least one gamma camera comprises mounting said at least one gamma camera further from said stationary portion than an x-ray CT imager.

* * * * *